US009068958B1

(12) United States Patent
Masuda et al.

(10) Patent No.: US 9,068,958 B1
(45) Date of Patent: Jun. 30, 2015

(54) USE OF SURFACE FREE ENERGY FOR DIFFERENTIAL EVALUATION OF CRYSTAL, CRYSTAL EVALUATED ON BASIS OF SURFACE FREE ENERGY AS INDEX, AND PHARMACEUTICAL COMPOSITION PREPARED BY CONTAINING THE CRYSTAL (71) Applicants: POLA PHARMA INC., Tokyo (JP); NIHON NOHYAKU CO., LTD., Tokyo (JP)

(72) Inventors: Takaaki Masuda, Kanagawa (JP); Hideo Kaneda, Tokyo (JP)

(73) Assignees: POLA PHARMA INC., Tokyo (JP); NIHON NOHYAKU CO., LTD., Tokyo (JP)

( * ) Notice: Subject to any disclaimer, the term of this patent is extended or adjusted under 35 U.S.C. 154(b) by 0 days.

(21) Appl. No.: 14/358,709

(22) PCT Filed: Apr. 30, 2013

(86) PCT No.: PCT/JP2013/063094
§ 371 (c)(1),
(2) Date: May 15, 2014

(87) PCT Pub. No.: WO2014/041846
PCT Pub. Date: Mar. 20, 2014

(30) Foreign Application Priority Data

Sep. 14, 2012 (JP) ................................. 2012-203028

(51) Int. Cl.
*G01N 33/15* (2006.01)
*C07D 409/06* (2006.01)
(52) U.S. Cl.
CPC .............. *G01N 33/15* (2013.01); *C07D 409/06* (2013.01); *C07B 2200/13* (2013.01)

(58) Field of Classification Search
CPC ...................................................... G01N 33/15
See application file for complete search history.

(56) References Cited

U.S. PATENT DOCUMENTS

2006/0286474 A1   12/2006   Morita et al.
2009/0030059 A1    1/2009   Miki et al.
(Continued)

FOREIGN PATENT DOCUMENTS

CN    103012385 A    4/2013
EP      0715856 A1   6/1996
(Continued)

OTHER PUBLICATIONS

Grimsey et al., "Analysis of the Surface Energy of Pharmaceutical Powders by Inverse Gas Chromatography," *Journal of Pharmaceutical Sciences*, vol. 91(2), pp. 571-583 (Feb. 2002).
(Continued)

*Primary Examiner* — Hezron E Williams
*Assistant Examiner* — David Z Huang
(74) *Attorney, Agent, or Firm* — Knobbe, Martens, Olson & Bear, LLP (57) ABSTRACT An object is to provide means for suppressing the formation of any isomer of luliconazole on account of any influence of, for example, the humidity and the light and improving the stability. Disclosed is a method for differential evaluating a crystal of luliconazole, comprising differential evaluating the crystal by using, as indexes, surface free energy of the crystal of luliconazole and a ratio of a polar component of the surface free energy, wherein the crystal is evaluated to be stable on condition that the surface free energy is smaller and the ratio of the polar component is lower.

2 Claims, 4 Drawing Sheets

$\gamma_L$ : surface tension of liquid $\gamma_S$ : surface tension of solid $\gamma_{SL}$ : solid-liquid interfacial tension (56) References Cited

U.S. PATENT DOCUMENTS

| | | |
|---|---|---|
| 2009/0076109 A1 | 3/2009 | Miki et al. |
| 2009/0137651 A1 | 5/2009 | Kobayashi et al. |
| 2010/0168200 A1 | 7/2010 | Masuda et al. |
| 2010/0173965 A1 | 7/2010 | Masuda et al. |
| 2010/0204293 A1 | 8/2010 | Masuda et al. |
| 2010/0210702 A1 | 8/2010 | Vontz et al. |
| 2012/0015997 A1 | 1/2012 | Miki et al. |
| 2012/0022120 A1 | 1/2012 | Kobayashi et al. |
| 2012/0149745 A1 | 6/2012 | Kobayashi et al. |
| 2012/0329845 A1 | 12/2012 | Masuda et al. |
| 2013/0011351 A2 | 1/2013 | Kobayashi et al. |
| 2013/0090365 A1 | 4/2013 | Kubota et al. |
| 2013/0096187 A1 | 4/2013 | Kobayashi et al. |
| 2014/0080882 A1 | 3/2014 | Masuda et al. |

FOREIGN PATENT DOCUMENTS

| | | | |
|---|---|---|---|
| EP | 2005958 A1 | 12/2008 | |
| JP | 9-100279 A | 4/1997 | |
| JP | 2002-114680 A | 4/2002 | |
| JP | 2004-341328 A | 12/2004 | |
| JP | 2005-223345 A | 8/2005 | |
| JP | 2007-024735 A | 2/2007 | |
| JP | 2007-147550 A | 6/2007 | |
| WO | WO 97/02821 A2 | 1/1997 | |
| WO | WO 2007/102241 A1 | 9/2007 | |
| WO | WO 2007/102242 A1 | 9/2007 | |
| WO | WO 2007/102243 A1 | 9/2007 | |
| WO | WO 2009/031642 A1 | 3/2009 | |
| WO | WO 2009/031643 A1 | 3/2009 | |
| WO | WO 2009/031644 A1 | 3/2009 | |
| WO | WO 2014/041708 A1 | 3/2014 | |
| WO | WO 2014/041825 A1 | 3/2014 | |
| WO | WO 2014/042043 A1 | 3/2014 | |
| WO | WO 2014/136282 | 9/2014 | |

OTHER PUBLICATIONS

Heng et al., "Wettability of Paracetamol Polymorphic Forms I and II," *Langmuir*, vol. 22(16), pp. 6905-6909 (Aug. 2006).

Niwano et al., "Efficacy of NND-502, a novel imidazole antimycotic agent, in experimental models of *Candida albicans* and *Aspergillus fumigatus* infections," *International Journal of Antimicrobial Agents*, vol. 12, pp. 221-228 (1999).

Shete et al., "Solid State Characterization of Commercial Crystalline and Amorphous Atorvastatin Calcium Samples," *AAPS PharmSciTech*, vol. 11(2), pp. 598-609 (Jun. 2010).

U.S. Appl. No. 14/263,293, Masuda et al.

USE OF SURFACE FREE ENERGY FOR DIFFERENTIAL EVALUATION OF CRYSTAL, CRYSTAL EVALUATED ON BASIS OF SURFACE FREE ENERGY AS INDEX, AND PHARMACEUTICAL COMPOSITION PREPARED BY CONTAINING THE CRYSTAL

TECHNICAL FIELD

The present invention relates to a crystal of luliconazole having a useful crystal habit as an active pharmaceutical ingredient for a pharmaceutical composition, and pharmaceutical compositions which contain the crystal as the active pharmaceutical ingredient.

BACKGROUND ART

Luliconazole is an antifungal agent which is excellent in the action on fungi. At present, luliconazole is widely used as a pharmaceutical or medicine for tinea pedis and tinea corporis, and it is going to be applied to tinea unguium as well. Further, luliconazole has an extremely high suppressing effect on *Aspergillus*. Therefore, it is also expected to be applied to profound mycosis (fungal disease) in a form of a pharmaceutical preparation (medicament preparation) for inhalation or the like for pneumonia and a vaginal agent for vaginitis. In relation to the pharmaceutical preparation of luliconazole, it is known as problems which should be solved that luliconazole is converted to stereoisomers, such as the SE isomer and the Z isomer, and that the crystallization of luliconazole is caused immediately after the application (see, for example, Patent Documents 1 to 6). In particular, as for the isomerization, the present inventors have confirmed that the stereoisomerization to the SE isomer or the Z isomer is influenced by the components of the pharmaceutical preparation, pH, the temperature, the humidity, and the light. Especially, the humidity and pH greatly affect the formation of the Z isomer. Therefore, it is necessary to provide any countermeasure thereagainst in relation to the pharmaceutical preparation which is to be used in a situation relevant thereto. For example, in the case of the tablet, the tablet must be stored for a long period of time under a wet or moist condition at low pH, for example, in gastric juice. In the case of the vaginal agent, the agent must be stored at a high humidity and low pH as well. It is doubtless that the inhalation should be used under a high humidity condition. It is clear that the formation of the Z isomer should be suppressed as far as possible during the period of time of the action. However, in the present circumstances, any effective measure should be inevitably found out by means of trial and error. On the other hand, it is known for the crystal or the like that the surface free energy is the factor which exerts any influence, for example, on the surface wetting characteristic (wettability) of the crystal or the like (see, for example, Patent Documents 7 to 10). However, it is not known at all that the surface free energy is changed depending on the condition of completion of an active pharmaceutical ingredient (crystal), and the change serves as an index for the stability or the like.

That is, it has been demanded to develop any means to improve the stability, for example, against the humidity, pH, and the temperature in relation to a crystal in a solid state or a pharmaceutical composition in a solid state prepared by using the crystal as described above.

Luliconazole

Z isomer

SE isomer

PRECEDING TECHNICAL DOCUMENTS

Patent Documents

Patent Document 1: WO2007/102241;
Patent Document 2: WO2007/102242;
Patent Document 3: WO2007/102243;
Patent Document 4: WO2009/031642;
Patent Document 5: WO2009/031643;
Patent Document 6: WO2009/031644;
Patent Document 7: JP2005-223345A;
Patent Document 8: JP2007-24735A;
Patent Document 9: JP2004-341328A;
Patent Document 10: JP2007-147550A.

SUMMARY OF THE INVENTION

Technical Problem

The present invention has been made in the circumstances as described above, an object of which is to provide means for suppressing the formation of any isomer of luliconazole on account of any influence of, for example, the humidity and the light and improving the stability.

Solution to Problem

Taking the foregoing circumstances into consideration, the present inventors have repeatedly performed diligent researches and efforts in order to seek for any means for suppressing the formation of any isomer of luliconazole on account of any influence of, for example, the humidity and the light. As a result, it has been found out that the surface free energy differs depending on the form of crystal, and the crystal, which has small surface free energy and which has a low ratio of a polar component of the surface free energy, is hardly affected, for example, by the humidity and the light, and thus the invention has been completed. That is, the present invention is as follows.

<1> A method for differential evaluation of a crystal of luliconazole, comprising:
evaluating the crystal by using, as indexes, surface free energy of the crystal of luliconazole and a ratio of a polar component of the surface free energy, wherein the crystal is evaluated to be stable on condition that the surface free energy is smaller and the ratio of the polar component is lower.

<2> The method as defined in <1>, wherein the surface free energy is not more than 28 mJ/m$^2$.

<3> The method as defined in <1> or <2>, wherein the ratio of the polar component of the surface free energy is not more than 35%.

<4> The method as defined in any one of <1> to <3>, wherein it is evaluated whether or not the crystal is suitable for a solid pharmaceutical preparation.

<5> A crystal which is evaluated to be highly stable in accordance with the method as defined in any one of <1> to <4>.

<6> A crystal of luliconazole which fulfills the following conditions 1 to 4:
(1) a ratio of a polar component of surface free energy of the crystal is not more than 31%;
(2) a dispersion component of the surface free energy of the crystal is not less than 18 mJ/m$^2$;
(3) the polar component of the surface free energy of the crystal is not more than 8.2 mJ/m$^2$; and
(4) the surface free energy of the crystal is not more than 27.4 mJ/m$^2$.

<7> A pharmaceutical composition comprising luliconazole which contains the crystal as defined in <5> or <6>.

<8> The pharmaceutical composition comprising luliconazole as defined in <7>, wherein the pharmaceutical composition is a solid pharmaceutical preparation.

<9> The pharmaceutical composition comprising luliconazole as defined in <7> or <8>, wherein the pharmaceutical composition contains a pharmaceutical preparation component which is appropriate to stabilize the crystal.

<10> A production method for producing a pharmaceutical composition comprising luliconazole, comprising a step of blending the crystal which is evaluated to be highly stable in accordance with the differential evaluating method as defined in any one of <1> to <4>.

<11> A pharmaceutical composition comprising luliconazole which is produced by the production method as defined in <10>.

Advantageous Effects of Invention

According to the present invention, it is possible to provide means for suppressing the formation of any isomer of luliconazole on account of any influence of, for example, the humidity and the light. That is, it is possible to provide means for improving the stability.

DESCRIPTION OF EMBODIMENTS

Abbreviations used in this specification are explained:
γs: surface free energy;
γs$^d$: dispersion component of surface free energy;
γs$^p$: polar component of surface free energy;
γs$^p$/γs: ratio of polar component of surface free energy.

<1> The Differential Evaluating Method of the Present Invention

The differential evaluating method of the present invention resides in a method for differential evaluating the stability of the crystal of luliconazole, characterized in that the surface free energy of the luliconazole crystal is measured to evaluate whether the stability is low or high on the basis of the magnitude of the surface free energy and the ratio of the polar component of the surface free energy. As for the stability in the differential evaluation as described above, the change of the contents of the isomer and the analog of luliconazole, in particular, the increment (increase in amount) of the content thereof is used as the index. The isomer of luliconazole is preferably exemplified by the SE isomer and the Z isomer as described above. Further, the present inventors have noticed the amide form which appears depending on the type of the solvent selected in relation to the luliconazole pharmaceutical preparation and which is an analog different from the SE isomer and the Z isomer. The amide form is not preferred as well in view of the decrease in the activity, and hence it serves as the index of the stability in the differential evaluation as described above.

Amide Form

Luliconazole, which is the objective of the differential evaluating method of the present invention, is an active pharmaceutical ingredient composed of crystal. According to the single crystal (monocrystal) X-ray diffraction analysis, the structure of the crystal resides in the crystal system, the space group, the lattice constant, and the R factor which substantially have the following values. At present, any form other than that of the following crystal system is not found in relation to luliconazole, and it is estimated that no polymorph exists.

Crystal system: Monoclinic; space group: P2$_1$; lattice constant: a=9.0171(9) Å, b=8.167(1) Å, c=10.878(1) Å, β=95.917(9)°; R factor: R=0.046, Rw=0.047.

The present inventors have noticed that the stability, especially the time-dependent changes of the Z isomer, the SE isomer, and the amide form differ depending on the production method in relation to the single crystal system of luliconazole as described above. Diligent investigations have been made about from what the difference in the stability depending on the production method originates. Surprisingly, it has been found out that the surface free energy of the crystal differs depending on any delicate or fine difference in the production method and/or the condition. The present invention has been made on the basis of the knowledge as described above.

The measurement of the surface free energy of the crystal may be performed in accordance with an ordinary method. For example, the contact angle with respect to the crystal is measured by means of the liquid penetration (permeation) rate measurement (machine type of apparatus: Processor Tensiometer K12, manufacturer: KRUSS GmbH) by using several solvents for which the surface free energy, the dispersion component of the surface free energy, and the polar component of the surface free energy are already known, and thus it is possible to perform the calculation therefrom by applying the model of Owens, Wendt, Rabel, and Kaelble. Preferred solvents for measurement in this method can be appropriately exemplified, for example, by n-hexane, tetrachloroethane, benzene, nitrobenzene, 1-nitropropane, and water. As for the method as described above, it is possible to make reference, for example, to a method described in Japanese Patent Application Laid-open No. 2010-183064.

That is, according to Examples described later on, a relationship of linear regression of $y=0.017x+0.03$ with a correction coefficient of 0.9 exists between the ratio (%) of the polar component of the surface free energy of the crystal of luliconazole and the formation rate of the Z isomer under a humidified condition. Further, the evident difference in the rate of occurrence (formation) of the Z isomer exists between 44% and 31% in relation to the ratio of the polar component of the surface free energy. It has been shown that the ratio of the polar component is preferably not more than 35% and more preferably not more than 31%.

Further, a relationship of linear regression of $y=-0.009x+0.25$ with a correction coefficient of 0.9 also exists between the dispersion component of the surface free energy and the formation rate of the Z isomer. The evident difference in the formation rate of the Z isomer exists between 18.4 mJ/m$^2$ and 16.1 mJ/m$^2$ in relation to the dispersion component of the surface free energy. The value is preferably not less than 17 mJ/m$^2$ and more preferably not less than 18 mJ/m$^2$.

A relationship of linear regression of $y=0.006x+0.03$ with a correction coefficient of 0.9 also exists between the polar component and the formation rate of the Z isomer. The evident difference in the formation rate of the Z isomer exists between 8.2 mJ/m$^2$ and 12.7 mJ/m$^2$ of the value. The value is preferably not more than 8.5 mJ/m$^2$ and more preferably not more than 8.2 mJ/m$^2$.

A relationship of linear regression of $y=0.012x-0.255$ with a correction coefficient of 0.9 exists between the surface free energy and the formation rate of the Z isomer. As for the value, the evident difference in the formation rate of the Z isomer exists between 27.4 mJ/m$^2$ and 28.8 mJ/m$^2$ of the value. The value is preferably not more than 28 mJ/m$^2$ and more preferably not more than 27.4 mJ/m$^2$.

That is, in relation to the surface free energy of the crystal, any one of the surface free energy itself, the dispersion component of the surface free energy, the polar component of the surface free energy, and the ratio of the polar component of the surface free energy can be used as the index for differential evaluation. It is preferable that the evaluation is performed while taking all of them into consideration.

That is, the preferred conditions are the following (1) to (4) in relation to the stability of the crystal, especially in relation to the stability of the crystal in order to provide the solid pharmaceutical preparation. When all of the conditions are fulfilled, the crystal is evaluated as being especially preferable.

(1) a ratio of a polar component of surface free energy of the crystal is not more than 31%;
(2) a dispersion component of the surface free energy of the crystal is not less than 18 mJ/m$^2$;
(3) the polar component of the surface free energy of the crystal is not more than 8.2 mJ/m$^2$; and
(4) the surface free energy of the crystal is not more than 27.4 mJ/m$^2$.

It is possible to estimate and confirm that the crystal of luliconazole, which has the property of the surface free energy as described above, is selected as a result of the execution of the differential evaluating method of the present invention.

The condition of the surface free energy in the crystal as described above greatly differs depending on, for example, the way of formation of the crystal, even in the case of the same solvent for the recrystallization. Therefore, it is preferable that the measurement is performed for every crystal to judge or distinguish whether the crystal is adequate or inadequate for the use as the active pharmaceutical ingredient for the pharmaceutical or medicine. The difference evidently exists between the recrystallization solvents. However, the other factors play considerable roles as well.

That is, a preferred production method for producing the pharmaceutical composition of the present invention is exemplified such that the production is performed by blending the crystal which is evaluated to be highly stable, where the crystal is evaluated in accordance with the differential evaluating method of the present invention.

<2> Crystal of the Present Invention

The crystal of the present invention resides in a crystal of luliconazole, which is characterized in that the crystal is evaluated to be highly stable in accordance with the differential evaluating method of the present invention described above. Those which are preferably usable as the crystal of the present invention satisfy any one of the following conditions. Those which fulfill all of the following conditions are especially preferable in the present invention.

(1) a ratio of a polar component of surface free energy of the crystal is not more than 31%;
(2) a dispersion component of the surface free energy of the crystal is not less than 18 mJ/m$^2$;
(3) the polar component of the surface free energy of the crystal is not more than 8.2 mJ/m$^2$; and
(4) the surface free energy of the crystal is not more than 27.4 mJ/m$^2$.

The crystal of the present invention, which fulfills the conditions as described above, exhibits such characteristics that the formation rate of the Z isomer as the isomer is low and the stability is high even in the case of a high humidity when the crystal is stored in a solid state. Therefore, the crystal of the present invention is preferred as an active pharmaceutical ingredient of a pharmaceutical preparation which is in a solid state and which is exposed to a high humidity. The pharmaceutical preparation, which is in a solid state and which is exposed to a high humidity, is preferably exemplified, for example, by oral administration pharmaceutical preparations including, for example, tablets, powders, capsules, and granules, inhalation pharmaceutical preparations, vaginal tablet pharmaceutical preparations, and vaginal suppository pharmaceutical preparations.

<3> Pharmaceutical Composition of the Present Invention

The pharmaceutical composition of the present invention is characterized in that the pharmaceutical composition contains the crystal of the present invention described above. When the pharmaceutical composition of the present invention is a solid pharmaceutical preparation, the content of the crystal of the present invention is preferably 5 to 95% by mass, more preferably 10 to 90% by mass, and much more preferably 20 to 80% by .mass. It is preferable that the pharmaceutical composition of the present invention is a solid pharmaceutical preparation in view of the characteristic thereof for the following reason. That is, even in the case of a liquid pharmaceutical preparation, the crystal can be maintained stably during a storage period until the production, which is preferred. However, in the case of the solid pharmaceutical preparation, the stability as the pharmaceutical preparation is improved as well.

The pharmaceutical composition of the present invention can contain any arbitrary component usable for ordinary medicines (pharmaceutical preparations) other than the crystal of the present invention described above. The arbitrary component as described above is preferably exemplified, for example, by excipient, binding agent, disintegrating agent, dispersing agent, taste/odor-correcting agent, extending agent, coating agent, plasticizer, and lubricant. The pharmaceutical composition of the present invention can be produced by treating the essential components and the arbitrary components as described above in accordance with an ordinary method. For example, in the case of the pharmaceutical composition having a form of granule, granules may be formed with a fluidized (powder) bed by using, for example, the crystal of the present invention, an excipient, a taste/odor-correcting agent, and a binding agent, followed by being sieved, graded (subjected to grading), and packaged. In the case of the tablet, graded granules may be subjected to tablet making (compression).

A pharmaceutical preparation component, which is preferred to stabilize the crystal, may be contained in the pharmaceutical composition of the present invention in view of the further improvement of the stabilization.

The pharmaceutical composition of the present invention is preferably used to treat or cure the disease caused by any fungus or prevent the deterioration of the disease by utilizing the characteristic of luliconazole. The disease caused by any fungus can be exemplified by profound mycosis (fungal disease) such as pneumonia and vaginitis Caused by the fungus, tinea pedis such as athlete's foot, tinea corporis such as candidiasis and tinea versicolor, and trichophytosis of hard keratin portion such as tinea unguium. The following dosage regimen is preferably available for the pharmaceutical composition of the present invention. That is, as for the administration route, it is possible to preferably exemplify, for example, oral administration, vaginal administration, inspiration or inhalation administration via trachea, and administration by injection. As for the dosage, it is preferable to use 10 to 10000 mg per day. The dosage differs in some cases depending on the administration route. It is possible to make reference to the amount of use of luliconazole usually used for the disease caused by any fungus.

The pharmaceutical composition of the present invention obtained as described above has such characteristics that the formation rate of the Z isomer is low and the pharmaceutical composition is stable even when the pharmaceutical composition is exposed to a high humidity.

EXAMPLES

The present invention will be explained in further detail below as exemplified by Examples. However, the present invention is not limited to Examples described below.

Example 1

Figure 1:
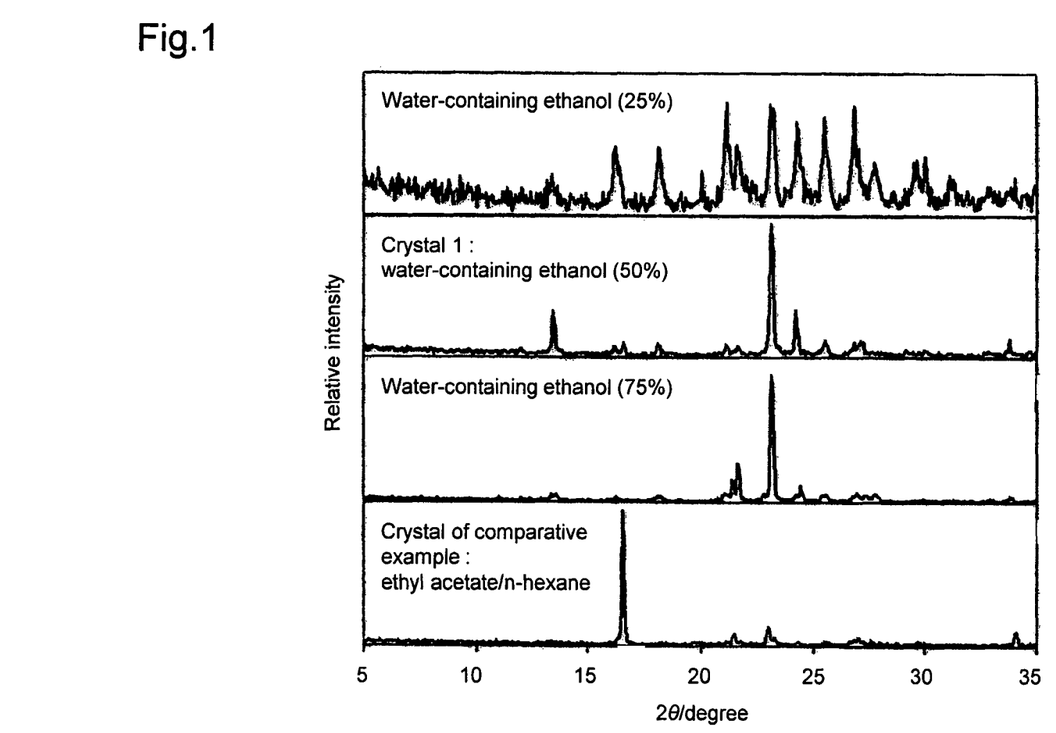
FIG. 1 shows results of powder X-ray diffraction measurement.
Figure 2:
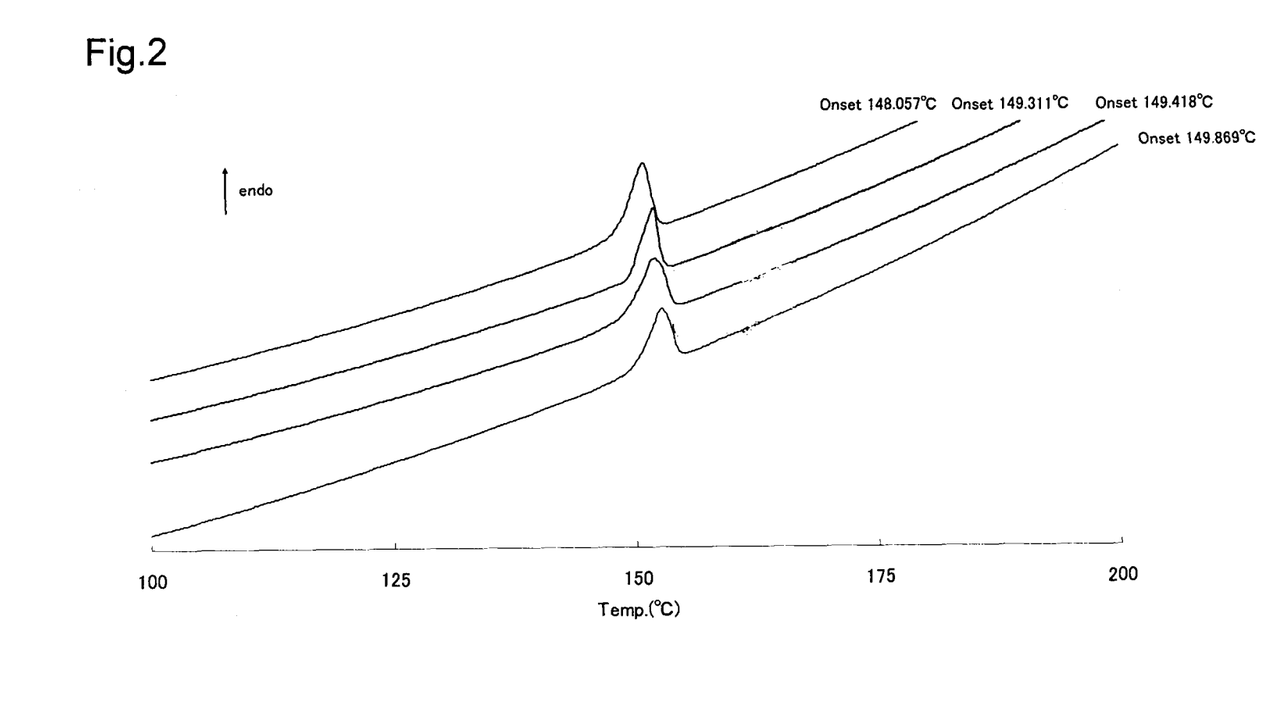
FIG. 2 shows results of DSC (differential scanning calorimetry).

Luliconazole was recrystallized under various conditions to obtain crystals in different states. The powder X-ray diffraction measurement was performed for these crystals (machine type of apparatus: XRD-DSCII, manufacturer: Rigaku Corporation, Condition: X-ray source: CuKα, measurement temperature: room temperature, tube voltage: 40 kV, tube current: 40 mA, 2θ: 5 to 35°, step angle: 0.05°). As a result, the positions of the diffraction angle 2θ of the diffraction peaks were identical in relation to all of them (see FIG. 1). Further, the peak was also single in DSC (machine type of apparatus: DSC7, manufacturer: PerkinElmer), and the melting point was observed in the vicinity of 149° C. (see FIG. 2, crystal recrystallized with water-containing ethanol (25%), crystal recrystallized with water-containing ethanol (50%), crystal recrystallized with water-containing ethanol (75%), and crystal recrystallized with ethyl acetate/n-hexane are shown from the top). According to these results, it is acknowledged that the crystal forms thereof are the same and any solvation does not exist as well.

Figure 3:
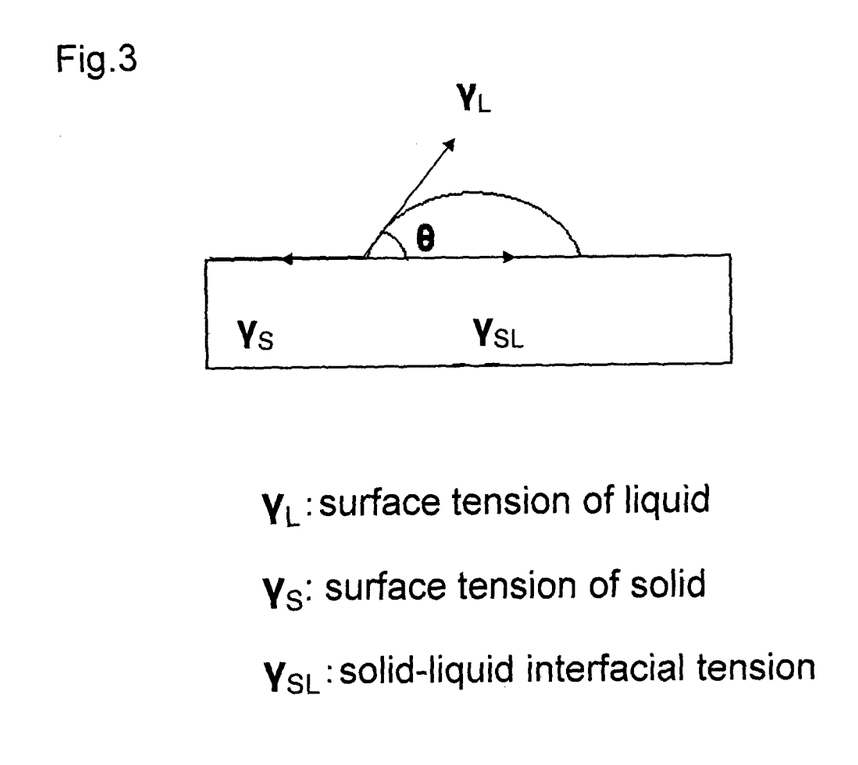
FIG. 3 shows the concept of the surface tension.
Figure 4:
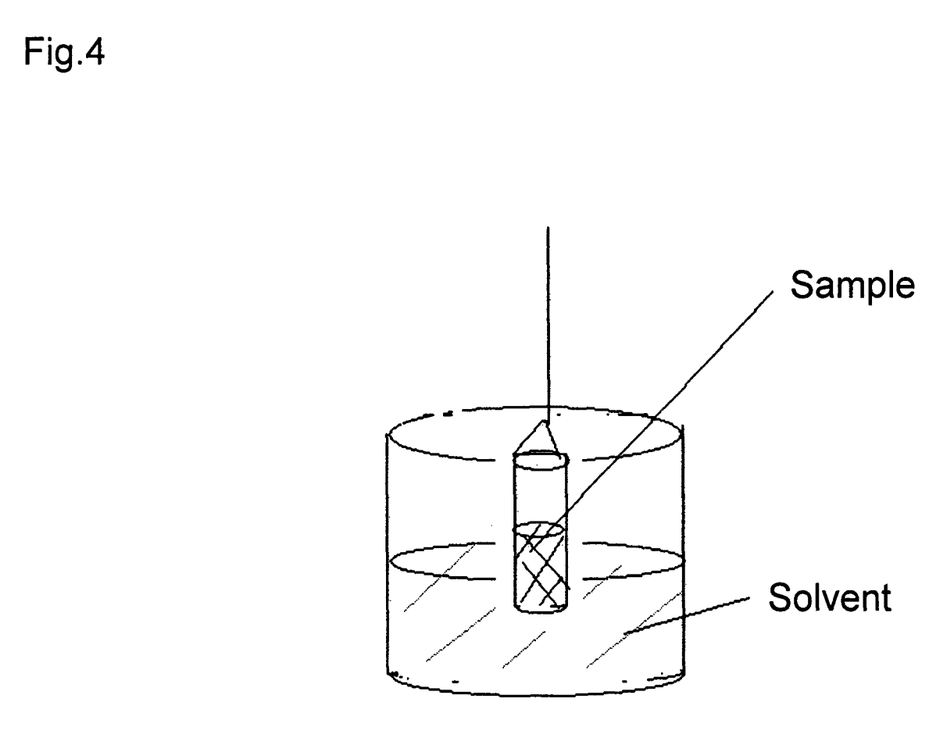
FIG. 4 shows a diagram of an apparatus for measuring the contact angle θ in Example 1.

In relation to the surface free energy, the contact angle θ is calculated in accordance with the Washburn's equation from the penetration (permeation) rate of liquid into powder obtained by the liquid penetration (permeation) rate measurement (machine type of apparatus: Processor Tensiometer K12, manufacturer: KRUSS GmbH). As for the surface free energy, the concept of Young's equation shown in FIG. 3 exists. The penetration (permeation) rate of the liquid in the chamber into the powder is measured by using a chamber tube shown in FIG. 4. From this result, the contact angle can be calculated utilizing Young's equation. Washburn's equation is represented by the following equation 1.

$$v = \frac{l^2}{t} = \frac{\gamma_L \cdot r \cdot \cos\theta}{2\eta} \qquad \text{Equation 1 (Washburn's equation)}$$

If this equation is converted into the weight of the solvent permeated into the powder per unit time, the following equation 2 is presented.

$$v = \frac{w^2}{t} = \frac{\gamma_L \cdot c \cdot \rho^2 \cdot \cos\theta}{\eta} \qquad \text{Equation 2}$$

The contact angle θ is determined by measuring the penetration (permeation) rate by using a solvent for which the surface tension ($\gamma_L$), the density ($\rho$), and the viscosity ($\eta$) of the liquid are known. The polar component and the dispersion component of the surface free energy are calculated in accordance with the Owens-Wendt-Rabel-Kaelble method by using θ thus determined. That is, assuming that the surface free energy is composed of the non-polar dispersion component $\gamma^d$ and the polar component $\gamma^p$, the following equations are presented.

$$\gamma_S = \gamma_S^d + \gamma_S^p$$

$$\gamma_L = \gamma_{L_d} + \gamma_{L_p}$$

$$\gamma_{SL} = \gamma_S + \gamma_L - 2\sqrt{\gamma_S^d \cdot \gamma_L^d} - 2\sqrt{\gamma_S^p \cdot \gamma_L^p} \qquad \text{Equation 3}$$

If Young's equation, which holds among the surface tension of the liquid, the surface tension of the solid, and the solid-liquid interfacial tension, is substituted with the above, the following equation is obtained.

$$\frac{1+\cos\theta}{2} \cdot \frac{\gamma_L}{\sqrt{\gamma_L^d}} = \sqrt{\gamma_S^p} \cdot \sqrt{\frac{\gamma_L^p}{\gamma_L^d}} + \sqrt{\gamma_S^d} \qquad \text{Equation 4}$$

The contact angle θ is determined, and plotted by using several types of solvents having known $\gamma_L$, $\gamma_L^d$, $\gamma_L^p$, and thus it is possible to determine $\gamma_S^p$ from the slope and $\gamma_S^d$ from the intercept. n-Hexane, tetrachloromethane, benzene, 1-nitropropane, and water were used as the known solvents. The values of $\gamma_L$, $\gamma_L^d$, $\gamma_L^p$ thereof are shown in Table 1 below.

TABLE 1

| | | Surface free energy (mJ/m²) | | |
|---|---|---|---|---|
| No. | Name of solvent | $\gamma_L^d$ | $\gamma_L^p$ | $\gamma_L$ |
| 1 | n-Hexane | 18.4 | 0.0 | 18.4 |
| 2 | Tetrachloromethane | 26.7 | 0.3 | 27.0 |
| 3 | Benzene | 26.7 | 1.7 | 28.4 |
| 4 | 1-Nitropropane | 25.5 | 3.9 | 29.4 |
| 5 | Water | 26.0 | 46.8 | 72.8 |

By utilizing the above, the surface free energy, the dispersion component of the surface free energy, the polar component of the surface free energy, and the ratio (%) of the polar component with respect to the surface free energy were calculated for samples (specimens) manufactured by the following methods.

Production Example 1

Luliconazole was dissolved in ethanol while being heated, to which water in an amount of 1/3 of that of ethanol was gradually added, followed by being gently cooled to obtain Crystal 1 (ethanol/water (75:25) not pulverized).

Production Example 2

Crystal 1 was ground or pulverized with an agate mortar for 3 minutes to obtain Crystal 2 (ethanol/water (75:25) pulverized for 3 minutes).

Production Example 3

Luliconazole was dissolved in ethanol while being heated, to which water in the same amount as that of ethanol was quickly added, followed by being quickly cooled to obtain Crystal 3 (ethanol/water (50:50)).

Production Example 4

Luliconazole was dissolved in ethyl acetate while being heated, to which n-hexane in the same amount as that of ethyl acetate was quickly added, followed by being quickly cooled to obtain Crystal 4 (ethyl acetate/n-hexane).

The surface free energy, the dispersion component of the surface free energy, the polar component of the surface free energy, and the ratio (%) of the polar component with respect to the surface free energy, which are calculated for Crystals 1 to 4, are shown in Table 2.

TABLE 2

| | | Surface free energy (mJ/m²) | | | $\gamma_S^p/\gamma_S$ |
|---|---|---|---|---|---|
| No. | Name of sample | $\gamma_S^d$ | $\gamma_S^p$ | $\gamma_S$ | (%) |
| 1 | Ethanol/water (75:25) not pulverized | 16.1 | 12.7 | 28.8 | 44 |
| 2 | Ethanol/water (75:25) pulverized for 3 minutes | 19.5 | 7.9 | 27.4 | 29 |
| 3 | Ethanol/water (50:50) | 18.4 | 8.2 | 26.6 | 31 |
| 4 | Ethyl acetate/n-hexane | 20.3 | 5.2 | 25.5 | 20 |

The storage testing under severely stressed condition was performed for Crystals 1 to 4. That is, each of the samples was suspended in water (infiltration condition or humidified condition), which was exposed to light at 6000 1× at 80° C. for 6 hours, followed by being collected by filtration and dried. After that, the ratio of the Z isomer of luliconazole with respect to the charging amount of luliconazole was measured and calculated. The measurement was performed by means of HPLC. The HPLC condition was as follows.
(HPLC condition)
Column: CHIRALCEL OD-RH 4.6×150 mm, column temperature: 35° C., mobile phase: mixture solution of methanol/1.8% aqueous solution of potassium hexafluorophosphate (83:17, v/v), flow rate: 0.56 mL/min., detection: 295 nm.

Results are shown in Table 3.

TABLE 3

| No. | Name of sample | $\gamma_S^p/\gamma_S$ (%) | Amount of formation of Z isomer (%) under condition of suspension in water and exposure to light |
|---|---|---|---|
| 1 | Ethanol/water (75:25) not pulverized | 44 | 0.11 |
| 2 | Ethanol/water (75:25) pulverized for 3 minutes | 29 | 0.08 |
| 3 | Ethanol/water (50:50) | 31 | 0.07 |
| 4 | Ethyl acetate/n-hexane | 20 | 0.07 |

The following facts are affirmed when the data is statistically processed.

1) A relationship of linear regression of y=0.017x+0.03 with a correction coefficient of 0.9'exists between the ratio (%) of the polar component and the formation rate of the Z isomer under a humidified condition in relation to the surface free energy. This fact means that the higher the ratio of the polar component is, the larger the amount of formation of the Z isomer is.

2) A relationship of linear regression of y=−0.009x+0.25 with a correction coefficient of 0.9 exists between the dispersion component and the formation rate of the Z isomer. This fact means that the larger the dispersion component of the surface free energy is, the more decreased the amount of formation of the Z isomer is.

3) A relationship of linear regression of y=0.006x+0.03 with a correction coefficient of 0.9 exists between the polar component and the formation rate of the Z isomer. This fact means that the larger the polar component of the surface free energy is, the more increased the amount of formation of the Z isomer is as well.

4) A relationship of linear regression of y=0.012x−0.255 with a correction coefficient of 0.9 exists between the surface free energy and the formation rate of the Z isomer. This fact means that the larger the surface free energy is, the more increased the amount of formation of the Z isomer is as well.

Example 2

Tablet 1 and Tablet 3 were prepared by using Crystal 1 (Production Example 1) and Crystal 3 (Production Example 3) of Example 1. That is, the tablets were prepared by mixing formulation components and then performing tablet making (compression) for 200 mg of the mixture at a tablet making (compression) pressure of 5 t/g in accordance with a direct tablet making (compression) method.

TABLE 4

| Component | % by mass |
|---|---|
| Granulated lactose | 50 |
| Luliconazole crystal | 50 |

Tablet 1 and Tablet 3 were stored for 24 hours under a condition corresponding to a humidity of 100% while being exposed to light (6000 1×) at 80° C. to carry out the storage testing under severely stressed testing. After carrying out the stressed testing, the amount of formation of the Z isomer and the amount of formation of the SE isomer of each of the tablets were quantitatively measured by HPLC. Results are shown in Table 5. Any numerical value indicates % by mass with respect to the charged crystal. Accordingly, the same tendency as that of the crystal was found in relation to the Z isomer. Such a tendency was found that the amount of formation of the Z isomer was more increased in relation to the tablet containing the crystal in which the surface free energy or the polar component of the surface free energy was large. On the other hand, a tendency which was not observed and was different from that of the crystal was found in relation to the SE isomer. It was revealed that the formation was more increased for the tablet containing the crystal in which the surface free energy was large or the polar component of the surface free energy was large.

As for the SE isomer, the storage testing under severely stressed testing was performed for the crystal in the same manner as the Z isomer. As a result, any difference was not observed in relation to the amount of formation depending on the difference in the crystal. That is, the tendency of the SE isomer was not observed for the crystal itself. It is suggested that the stability may be possibly more suppressed in the case of those relevant to the pharmaceutical preparation as compared with the crystal itself. This also means, vice versa, that it is important for the solid pharmaceutical preparation to maintain a more stable form in relation to the crystal.

TABLE 5

| Sample | Z isomer | SE isomer |
|---|---|---|
| Tablet 1 | 0.08 | 0.09 |
| Tablet 3 | 0.04 | 0.04 |

INDUSTRIAL APPLICABILITY

The present invention can be applied to the pharmaceutical.

The invention claimed is:

1. A method for differential evaluation a crystal of luliconazole, comprising:
    evaluating the crystal by using, as indexes, surface free energy of the crystal of luliconazole and a ratio of a polar component of the surface free energy, wherein the crystal is evaluated as that formation rate of the z isomer is low and the crystal is suitable for a pharmaceutical preparation on condition that the surface free energy is not more than 28 mJ/m$^2$ and the ratio of the polar component of the surface free energy is not more than 35%.

2. The method according to claim 1, wherein the crystal is evaluated to be suitable for a solid pharmaceutical preparation.

\* \* \* \* \*